United States Patent [19]

Katzer et al.

[11] Patent Number: 5,279,150
[45] Date of Patent: Jan. 18, 1994

[54] AUTOMATED MINIATURE CENTRIFUGE

[76] Inventors: Albert E. Katzer, 1940 Winifred St., Cheboygan, Mich. 49721; Rodney A. Katzer, 12 Elm St., R.D. #4, Chester, N.J. 07930; Charles F. McBrairty, 2801 Northampton St., Easton, Pa.

[21] Appl. No.: 851,183

[22] Filed: Mar. 13, 1992

[51] Int. Cl.$^5$ .......................... G01N 21/07; B04B 1/04
[52] U.S. Cl. .................... 73/61.66; 73/61.69; 356/39; 356/435; 356/440; 356/246; 422/72; 436/45; 436/70; 494/10; 494/16
[58] Field of Search ................ 73/61.63, 61.65, 61.66, 73/61.68, 61.69, 61.71, 64.56, 61.41, 61.43; 250/265, 273, 275, 276, 277; 356/39, 435, 436, 246, 440, 428; 436/10, 16, 45, 70, 72; 422/101, 82.05, 82.09; 128/760, 770; 604/317; 494/10, 16

[56] References Cited

U.S. PATENT DOCUMENTS

| | | | |
|---|---|---|---|
| D. 259,140 | 6/1981 | Pross et al. | D24/22 |
| 3,679,367 | 7/1972 | Negersmith et al. | 73/61.65 |
| 3,807,874 | 4/1974 | Gropper | 356/436 |
| 3,937,581 | 2/1976 | Rödel et al. | 494/10 |
| 4,115,011 | 9/1978 | Brunsting | 356/246 |
| 4,128,400 | 12/1978 | Mühlböck et al. | 422/72 |
| 4,640,896 | 2/1987 | Farrell et al. | 422/72 |
| 4,680,475 | 7/1987 | Tansony et al. | 356/435 |
| 4,683,579 | 7/1987 | Wardlaw | 356/39 |
| 4,695,164 | 9/1987 | Zivitz et al. | 356/246 |

FOREIGN PATENT DOCUMENTS

| | | | |
|---|---|---|---|
| 4036048 | 5/1991 | Fed. Rep. of Germany | 73/61.69 |
| 1214144 | 4/1960 | France | 73/61.63 |
| 58-160843 | 9/1983 | Japan | 73/61.66 |

Primary Examiner—Hezron E. Williams
Assistant Examiner—Michael Brock
Attorney, Agent, or Firm—Eckert Seamans Cherin & Mellott

[57] ABSTRACT

A measurement device is provided for determining relative proportions of at least two materials forming a liquid and having different densities and different responses to light. A transparent capillary size cuvette tube confines the sample liquid, and is attached radially on a rotor wheel, preferably by a holder which seals an outer end of the tube and provides a package for manipulation of the tube without exposure to the sample. A motor controlled by a processor turns the rotor wheel, separating the materials by their densities. A linear light source illuminates the tube, and a linear array of photosensors defining pixels produces a signal which varies where the different materials abut. The pixels are counted, to locate the stratum between materials and the result is displayed as a percentage of total volume, suitable for hematocrit measurements. The cuvette tube has a fin for assisting in manipulation, is shaped as an elongated lens, and is cut to a spherical end surface to assist in sample collection.

10 Claims, 2 Drawing Sheets

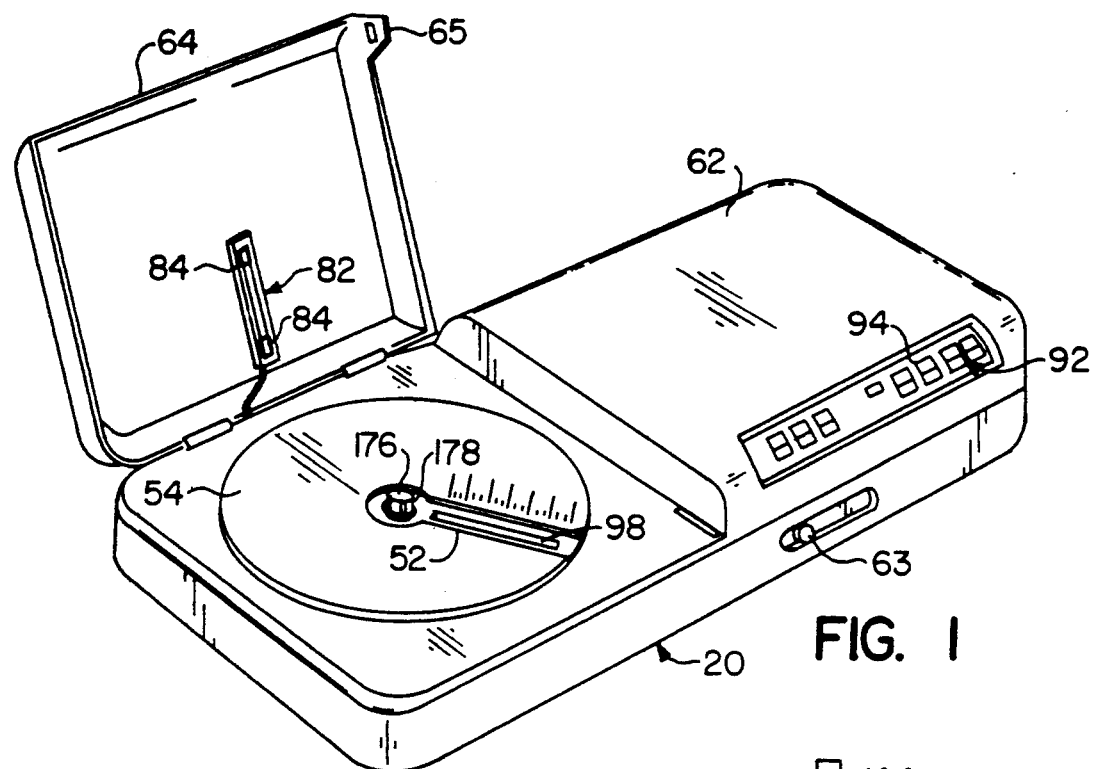
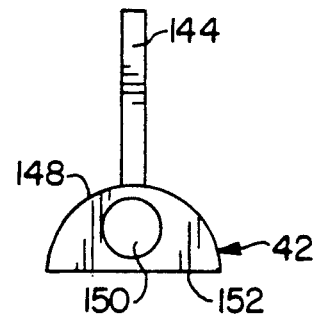
FIG. 3
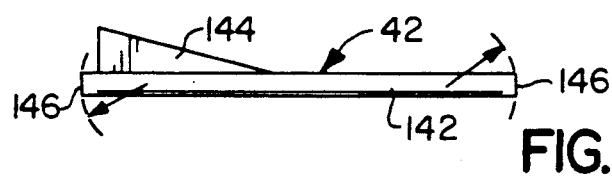
FIG. 2
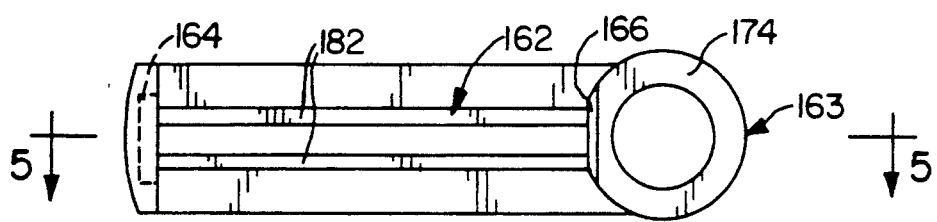
FIG. 4

AUTOMATED MINIATURE CENTRIFUGE

FIELD OF THE INVENTION

This invention relates to the centrifuges, especially for separating component parts of blood samples contained in capillary tubes. The invention provides a novel form of capillary tube, holder therefor, and centrifuge for separating the components, operable automatically to centrifuge one or more samples and to take a hematocrit measurement or the like. The device rotates samples around an axis and optically detects the position of the line between separated components, converting the detected position into a numerical display of proportionate volume of the sample up to the line.

PRIOR ART

Miniature centrifuges are known for preparing blood samples for certain tests. An example is shown in U.S. Pat. Des. No. 259,140. Hematocrit determinations normally require centrifuging blood samples, usually carried in capillary tubes. The proportion of corpuscles to plasma in the sample can be seen and measured after separating the denser opaque corpuscles from the less-dense clear plasma. Apart from hematocrit measurement, blood plasma extractions for other purposes are also possible by centrifuging.

A standard procedure is to rotate radially-oriented capillary tubes around the axis of a motor shaft, for example for 3 minutes at around 10,000 revolutions per minute. It is necessary to seal the radially outward end of the capillary tubes. The more-dense solid constituents of the blood (especially the red blood cells) become packed at the outward end under sustained centripetal acceleration, displacing the plasma to the radially inner end. The packed blood cells occupy a length along the tube which can be compared to the total length of the sample to determine the proportion of corpuscles to total volume, this percentage being the typical expression of a hematocrit measurement. In a miniature centrifuge, a graduated scale can be provided adjacent a mounting means for the capillary tube holding the sample. The tube is filled with the blood sample (100% on the scale), centrifuged, and the user reads the hematocrit percentage from the scale at the line at which the packed red blood cells and the substantially clear plasma abut.

A plurality of samples can be centrifuged simultaneously. U.S. Pat. No. 4,052,164 —Konig discloses a rotor with symmetrically arranged radial channels for receiving tubular containers of blood or other material. One end of the container is placed in a receiving groove associated with the hub of the rotor. The other end of the tube is placed against a resilient abutment at the circumference of the rotor.

U.S. Pat. Nos. 4,052,165 Wienchol et al; and 4,193,538 Schwartz disclose centrifugal apparatus wherein radially outer ends of a number of capillary tubes are placed against a resilient sealing flange at the circumferential edge of the rotor. The radially inner ends are placed against a clamping hub which has a limited axial displacement. Inasmuch as the capillary tubes are inclined relative to the plane of the rotor as so placed, axial displacement of the clamping hub toward the rotor presses the capillary tubes radially outwardly against the sealing flange. The hub has a latching mechanism holding the clamping hub in the locked or released position. The hematocrit reading can be obtained from scales disposed at each tube location.

Centrifuges, including miniature ones, can include means for sensing the rate of rotation of the rotor, and for reading out the rate. Sensing means are appropriate in centrifuges which are provided with speed controls allowing the sample to be rotated more or less vigorously, particularly because for repeatable results or for making comparisons between samples, the samples should be processed in a similar manner.

Known miniature centrifuge devices require that the technician manually handle the sample tube for collecting the sample, for placing it in the centrifuge and for removing it after the test. The capillary tubes used are simple clear tubes of glass or plastic. The thickness of the walls of the tube is generally the minimum necessary to prevent accidental breakage, and the walls define cylindrical surfaces on the inner and outer sides. The tubes are open at both ends and are relatively small in diameter. The technician fills a tube by manually touching one of the two ends to a droplet of blood drawn from the user, for example at a pin prick in the finger, earlobe or the like. Surface tension draws the blood into the tube by capillary action and maintains it in place under normal conditions. However, the force developed in centrifuging is sufficient to overcome surface tension holding the sample in the tube, and accordingly at least one end of the tube must be sealed during the centrifuging operation.

Capillary tubes may be provided in different lengths and different volumes for different tests, provided that the lumen of the capillary tube is sufficiently small that surface tension of the blood keeps it in place. It is unnecessary to carefully measure the amount of blood in the sample because the lumen always fills provided there is a sufficient volume in the droplet from which the sample is drawn. For example, a 9 $\mu l$ capillary may be appropriate for hematocrit tests and a 30–60 $\mu l$ volume tube for plasma extraction.

Inasmuch as the capillary tube is open at the ends, there is a danger of contamination or spread of infectious disease associated with hematocrit measurements. The small size of the tube may make it difficult to grasp and manipulate under all circumstances. Additionally, the small internal diameter of the tube produces a relatively small line of packed red blood cells. Although the delineation between the red blood cells and the plasma is usually well defined, it would be advantageous to improve its visibility, or better yet to avoid the need to view the line to obtain a measurement. It would further be desirable to obtain these objects using a sample tube or cuvette which can more easily be manipulated and which, notwithstanding the necessity for open tube ends, better protects the technician from exposure to the sample.

SUMMARY OF THE INVENTION

It is an object of the invention to automatically process blood separations and measurements such as hematocrit measurements in an inexpensive, compact and accurate article of test equipment.

It is also an object of the invention to provide a numerical output of a hematocrit test, with a minimum of input required of the technician running the test.

It is a further object of the invention to provide an improved form of capillary tube adapted for easy filling, manual insertion in a carrier, and automated testing.

It is another object of the invention to provide an intermediate carrier for a capillary tube which forms a sealing receptacle and which readily engages on the rotor of a centrifuge, the carrier being manipulated by manually grasping a fin protruding from the capillary tube in the receptacle.

These and other objects are accomplished by a measurement device according to the invention for determining relative proportions of at least two materials forming a liquid and having different densities and different responses to light. A transparent capillary size cuvette tube confines the sample liquid, and is attached radially on a rotor wheel, preferably by a holder which seals an outer end of the tube and provides a package for manipulation of the tube without exposure to the sample. A motor controlled by a processor turns the rotor wheel, separating the materials by their densities. A linear light source illuminates the tube, and a linear array of photosensors defining pixels produces a signal which varies where the different materials abut. The light source and photosensors can be on opposite sides of the rotor having an opening at the sample, for taking a measurement as the sample passes. The pixels on one side of the demarcation line between the materials (i.e., the light ones or the dark ones) are counted. The result is displayed as a percentage of total sample volume, suitable for hematocrit measurements. The cuvette has a protruding fin for assisting in manipulation. The tube portion of the cuvette is shaped as an elongated lens, and is formed to a spherical end surface to assist in sample collection.

The rotor preferably defines an opening along a range where the stratum between the materials is expected, normally the full range of 0 to 100% of sample length; however a reflective rather than transmissive arrangement is also possible. The radiation used is preferably infrared light.

The source of radiation can be one or more LEDs arranged to illuminate an elongated radial line on the rotor, and the sensor can include a line of light sensitive diodes, charge coupled devices or the like, which develop a voltage charge as a function of illumination. The respective charges can be shifted to a threshold detector means for encoding light levels at the pixels and comparing the light encoded light levels for localizing the stratum between separated materials. These functions are effected under control of the processor, which also controls and times the motor to process the samples accurately in a programmed manner, and calculates and displays the results numerically.

The angular position of the rotor can be sensed using one of the photosensors for triggering the radiation sensing means at a position where the opening in the rotor where the sample is carried is disposed between the light source and the radiation sensing means. Alternatively, a reflective sensor can be used. In the event that a plurality of samples are to be tested simultaneously, a plurality of sample holders and angular position detectors can be arranged on or about the rotor.

BRIEF DESCRIPTION OF THE DRAWINGS

There are shown in the drawings the embodiments that are presently preferred. It should be understood, however, that the invention is not limited t the precise arrangements and instrumentalities shown, and is capable of other configurations and groupings of components. In the drawings, FIG. 1 is perspective view of a miniature centrifuge according to the invention, however, with the cuvette and cuvette holder removed.

FIG. 2 is a side elevation view of a cuvette according to the invention, for carrying a sample.

FIG. 3 is an end elevation view of the cuvette according to FIG. 2, in a larger scale.

FIG. 4 is a plan view of a cuvette holder for handling the cuvette and for mounting the cuvette on the rotor of the centrifuge.

DETAILED DESCRIPTION OF THE PREFERRED EMBODIMENTS

Figure 5:
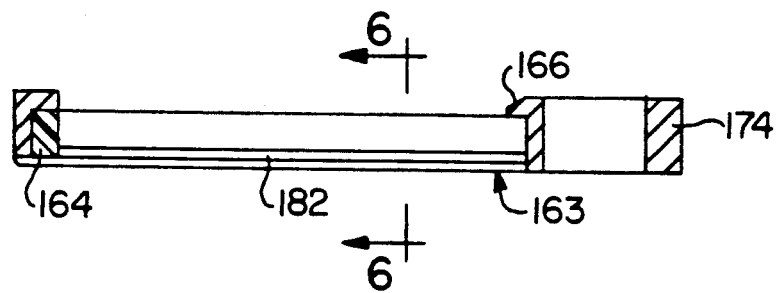
FIG. 5 is a section view through the cuvette holder, taken along line 5—5 in FIG. 4.

Referring to FIG. 1, the automated centrifuge 20 according to the invention is a measurement apparatus for determining relative proportions of at least two materials forming a liquid and having different densities. In connection with blood testing and plasma separation, the two materials of interest are corpuscles and clear plasma. The two materials have different properties with respect to transmission, absorption and reflection of radiation such as infrared light, and this aspect can be used to discriminate between the corpuscles and the plasma after the sample has been centrifuged to pack the corpuscles 32 at one end of the cuvette or other container in which the sample is carried, displacing the plasma 34 to the other end.

At least one cuvette 42 or similar container can be mounted on the centrifuge, confining a sample of liquid to be tested. According to the preferred embodiment shown, a receptacle 52 is provided for one sample o the rotor 54 of the centrifuge 20. It will be appreciated that two or more samples could be centrifuged at the same time, and all or only one can be measured automatically according to the invention.

A rotor wheel 54 is provided in a housing 62, preferably arranged to be enclosed by a housing cover 64 which can lock closed by interaction of a slidable locking tenon which can be associated with an on/off slide switch 63 and a locking opening in a tab 65, engaged by the tenon when the cover 64 is closed. The rotor wheel 54 has means for holding the cuvette 42 such that it defines a length extension oriented radially of an axis of rotation 66 of the rotor wheel, and is held radially inwardly relative to the axis. A motor 68 (see FIG. 7) is coupled to the rotor wheel for rotating the rotor wheel and the cuvette about the axis, whereby the materials of different densities, i.e., blood cells and plasma, are separable along the length extension due to centripetal acceleration relative to the axis. The motor can be operated, for example, at 10,000 to 12,000 revolutions per minute, for a period of three minutes, whereupon the blood cells and the plasma become separated substantially to occupy different positions along the length extension. Whereas the plasma 34 is clear and the blood cells 32 are opaque, a well defined stratum line 70 is defined between the materials after separation. In a sample having a higher or lower proportion of blood cells, the position of the stratum line along the radius varies accordingly.

At least one source of radiation 82 is arranged to illuminate the cuvette 42 along at least a portion of the length extension. It is preferable to illuminate the entire length of the sample in the cuvette. It is also possible, however, to assume that all the samples to be measured will fall within some range, and to illuminate and discriminate for the stratum line over a shorter length encompassing the expected range of variation.

A number of variations are possible for sources of illumination. According to the embodiment shown in FIG. 1, two LEDs 84 which can have associated lenses or diffusers to concentrate light emission along the sample, are disposed on the lid 64 of the housing 62 such that when the lid is closed the LED direct light downwardly toward the sample, for example from a distance of about one cm (about half an inch). Preferably the illumination is infrared light on the order of 200–600 nm wavelength. The sample could be illuminated by a more widespread general illumination of the rotor area, or a scanning illumination means could be provided, such as a rotating mirror arrangement. Illumination in the manner shown is preferred as it dissipates little power, is simple and inexpensive, and provides a sharp distinction between the blood cells and the plasma.

Radiation sensing means 86 is provided to detect radiation passing through the sample from the source of illumination over at least a range along the portion of the length extension which is illuminated. The radiation sensing means can be operable to sense light transmitted through the sample or reflected from the sample. Alternatively, the sensing means can be scanned. The sensing means 86 produces a signal as a function of the transparency/opacity (or in a reflective arrangement the absorption/reflection characteristics) of the sample along the line of extension, i.e., along the radial line encompassed by the sample. Preferably, the illumination means 82 and the sensing means 86 are disposed on opposite sides of the sample, and thus respond to the transparency/opacity of the sample.

An indicator 92 is provided to read out the signal for displaying a relative position in the range of a stratum 70 between the materials, defined by the signal. The indicator 92 shows the position in the range of the detected change in optical characteristics of the sample which identifies the boundary between the materials. Preferably the indicator produces a numeric readout; however it is also possible that the position could be displayed graphically.

Figure 7:
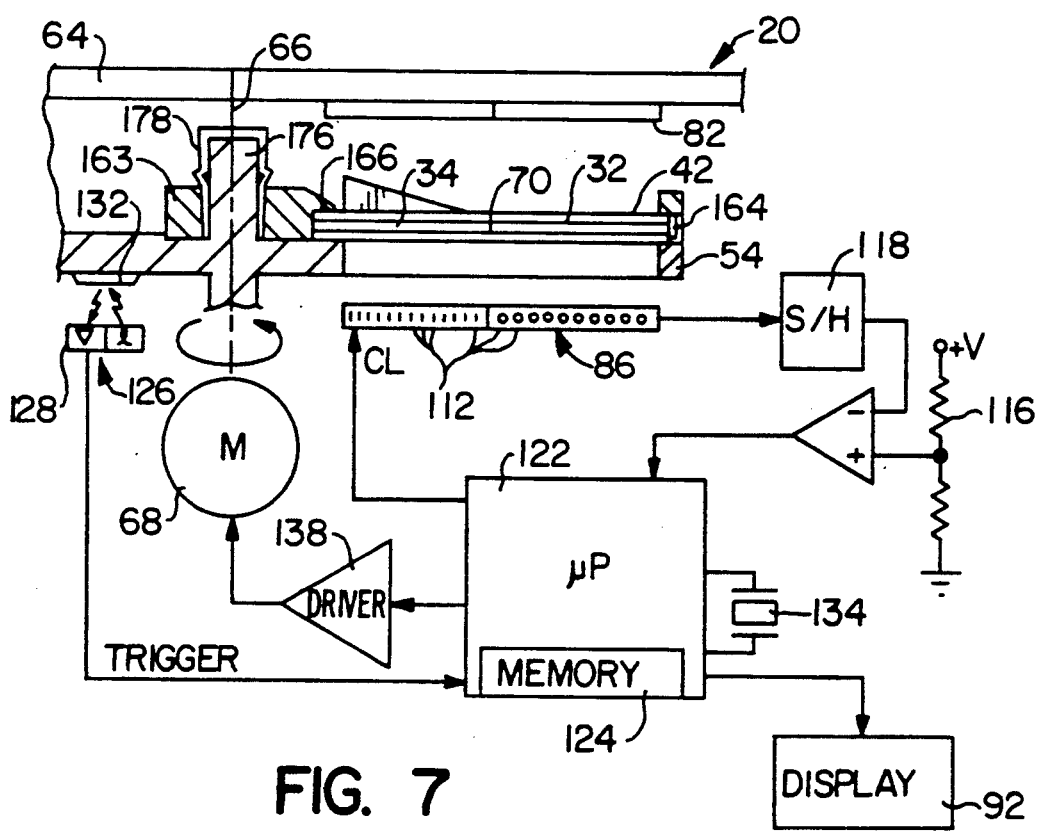
FIG. 7 is a schematic illustration showing operation of the centrifuge to take an automated hematocrit measurement.

As shown in FIG. 7, the light source 82 and the light sensor 86 are preferably placed on opposite sides of the rotor 54, and the sample passes between them with each revolution of the rotor. The rotor defines an opening 98 along the range for viewing through the cuvette 42 and the sample therein. The sensor 86 preferably comprises an elongated array of light sensitive elements 112 defining discrete pixel positions. These elements can be photodiodes, elements of a charge-coupled device array (CCD) or the like, operable to develop a voltage signal as a function of the level of sensed illumination. The level of the signal at each pixel element 112 is encoded. Preferably, the level is compared to a threshold level, for determining whether the pixel is illuminated (through the plasma) or occluded (by the blood cells). The threshold level can be fixed, for example via a voltage divider 116 coupled to an amplifier to form a comparator, or circuitry can be provided to set the threshold adaptively as a function of average light level. For example two storage capacitors can be charged respectively during the light and dark intervals, and the accumulated voltages averaged by a voltage divider to determine the mean light level between light and dark pixels for use as the threshold.

The voltages of the pixel elements also can be encoded using an A to D converter. In the embodiment shown, the signal levels are coupled to a sample and hold circuit 118, which may include an amplifier, and compared to a fixed reference by a comparator. The pixel levels are shifted through to the sample and hold, or alternatively, a separate threshold detecting circuit can be arranged for each pixel.

The number of pixels defines the precision of measurement. Preferably, in connection with a cuvette illuminated along 100% of a length of about 3.2 cm (1.25 inches), 256 pixels are provided, resulting in a precision of ±0.4%. The pixels may be directly in line, or may be staggered to allow a larger number to fit within a given length extension. The results of the threshold detection for each pixel defines a binary bit. A digital processor 122 and timing means are coupled to the signal, allowing the processor (or a separate counter) to count pixels on at least one side of a change between high and low light levels defining the position of the stratum, and to calculate a percentage of the range occupied by pixels on that side relative to a total number in the range. The processor can be an Intel 8051C processor, including appropriate memory 124 for program and data storage, which is coupled to a display such as an LED or liquid crystal seven segment or alphanumeric display, whereby the results or the hematocrit measurement or the like are displayed numerically as the percent volume of corpuscles to total sample volume.

The sensing device preferably operates to read incident light levels only when the sample is in the appropriate position over the detectors. It is also possible to use peak detection techniques to selectively collect data while the sample is in place, and to ignore any levels detected when the sample is not between the light source and the detectors defining the pixels. According to the embodiment of FIG. 7, a trigger device 126 is coupled to the processor 122 for enabling data to be collected only when the opening 98 in the rotor 54 (and therefore the sample) are disposed between the source 82 and detectors 86. The trigger has a further source/detector arrangement 128 which senses the passage of a reflective spot 132 on the underside of the rotor 54. The reflective spot 132 is in position to trigger the source/detector package when the sample is in position. The source/detector arrangement 128 can be located at any point on the rotor, e.g., on the underside or edge, provided the reflective spot is correspondingly positioned to provide a trigger signal when the opening is in place.

The triggering mechanism 126 also provides an indication of rotation of the rotor. The processor 122 can count revolutions by counting trigger signals. The processor also monitors passage of time, e.g., by counting down its clock signal as based on crystal 134 or by monitoring a counter coupled to the clock signal. The rotational speed of the motor can be averaged over a number of revolutions, or for a predetermined time period. The RPM level sensed and the elapsed centrifuging time can be shown on the display.

The processor controls operation of the motor via driver 138. Preferably, the processor is arranged to set the motor to maintain one of at least two rotational speeds, including a centrifuging speed of about 10,500

RPM, and a reading speed, e.g., about 200 RPM. Switch inputs to processor 122 (not shown) can be provided for allowing the technician to select among different centrifuging processes. The processor is preferably programmed to maintain the centrifuging speed for a long enough time to pack the corpuscles 32, e.g., three minutes, then to drop to a slower reading speed. At the reading speed, the processor preferably repetitively determines the stratum point 70 between the corpuscles 32 and the plasma 34, and averages the result.

The invention is operable using a variety of container types. However the container is preferably a capillary tube cuvette having an inner diameter elongated along the length extension, sufficiently small to retain the liquid sample via surface tension, and wherein the means for holding the container includes a cuvette holder operable to seal at least a radially outer end of the cuvette, the rotor having means for engaging the cuvette holder to position the cuvette along the radial extension. An internal diameter of about 1.5 mm (0.06 inch) is an appropriate internal diameter. The cuvette can be on the order of 3.2 cm (1.25 inch) in length. It is also possible to use a longer cuvette arrangement, for example if the cuvette is used to collect separated plasma, or if better accuracy in hematocrit percentage is needed.

A preferred form for the cuvette 42 is shown in FIGS. 2 and 3. The cuvette has an elongated capillary tube portion 142 and a fin 144 arranged to extend axially upwardly from the rotor 54 as the cuvette 42 is held relative to the rotor, the fin assisting in manual manipulation of the cuvette, which is rather small. The fin 144 is arranged at an end of the cuvette and is inclined toward the tube portion 142 in a direction approaching an opposite end. This arrangement is characterized by a relatively smaller thickness of material near the center of the cuvette 42 than near the ends, making it easier to view through the cuvette in the area where the junction between the plasma and the corpuscles is likely to fall. The fin arrangement increases the area available for the technician to grasp and manipulate the cuvette, and thus reduces the possibility it will be dropped or fumbled with potential exposure of the technician to the sample.

At least one end of the cuvette, and preferably both ends, are formed to a spherical surface 146 as shown by broken lines in FIG. 2. The spherical surface is such that when the cuvette is placed endwise against a flat surface (such as the patient's skin), a tapering capillary inlet to the lumen of the cuvette is defined between the flat surface and the end of the cuvette. Where the flat surface has a droplet of blood from a pin prick in the skin or the like, from which a sample is to be loaded into the cuvette, the spherical surface aids the establishment of a capillary passageway into the lumen for causing surface tension to draw the sample into the cuvette.

In order to make the sample in the cuvette more visible, the outer diameter of the tube portion of the cuvette is shaped as an elongated lens rather than being cylindrical. This aspect of the invention is best shown in FIG. 3. In cross section the cuvette tube has an arched side 148 having a larger external diameter than the lumen 150, and a flat side 152 opposite from the arched side. The arched side 148 is not concentric with the lumen 150, instead having a center which is approximately at the plane of the flat side 152, i.e., displaced laterally from the center of the lumen. Radiation from the source 82 is concentrated on the sample according to this arrangement. Light passing perpendicularly through the cuvette encounters the thinnest walls (a the top and bottom of the cuvette as shown in FIG. 3). Refraction of light diverging from the source bends rays inwardly toward the lumen 150. Additionally, a person viewing the sample in the lumen laterally, from an angle off the centerline defined by the fin 144, perceives the sample as magnified. This arrangement is therefore advantageous for both viewing and automatic measurement.

Figure 6:
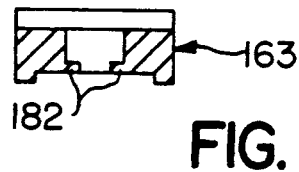
FIG. 6 is a section view taken along line 6—6 in FIG. 5.

The flat side 152 is used as a base for the cuvette, being oriented toward the radiation sensing means 86 and resting on a flat depression 162 in a carrier 163 which is arranged to lock onto the rotor 54. The cuvette holder 163 as shown in FIGS. 4-6 is dimensioned to receive and sealingly engage the cuvette 42. A compressible seal 164 of rubber or plastic is disposed at one end of a receptacle for the cuvette defined in the top of the holder. A clasp means comprising a tapered beak 166 is formed at an opposite end of the receptacle, and the cuvette holder has abutments at the ends of the receptacle arranged such that when the cuvette is pressed endwise against the seal and passed laterally over the tapered clasp means, the cuvette snaps into place and is held in the cuvette holder with the seal 164 compressed by the end of the tube portion 142 of the cuvette 42. The cuvette 42 and the cuvette holder 163 then can be manipulated readily, using the fin 144 or the holder 163 to grasp the cuvette while confining the body fluid samples to the cuvette. The spherical end surface 146 disposed against the seal 164 also tends to improve sealing in that this shape is characterized by a protruding relatively sharper center portion immediately adjacent the lumen 150, which engages well with the seal 164.

Referring to FIGS. 1 and 4, the cuvette holder 163 fits into a complementary shaped depression 52 in the rotor 54, and the hub portion 174 of the cuvette holder 163 slips over the shaft portion 176 of the rotor. A spring clip 178 having radially protruding bumps can latch the holder 163 onto the shaft. Alternatively or in addition, a threaded cap (not shown) can engage over the shaft.

FIG. 7 shows the cuvette, cuvette holder, rotor, light source and detectors in operative arrangement with the cuvette in the holder and the holder in the rotor. FIGS. 5 and 6 illustrate the holder 163 in cross sectional views taken from FIG. 4. The holder has a shelf formed by flanges 182 extending laterally inwardly, with a space between the flanges of the approximate size of the lumen of the cuvette. When snapped past beak 166, the cuvette 42 is securely placed, sealed on the radially outward end, and ready for centrifuging or other handling. The holder 163 can be a disposable item, which forms a permanent holder for the cuvette and is discarded with the cuvette. The holder 163 is removed from the rotor 54 by grasping the radially outermost end of the holder and lifting, which pops the holder from the rotor shaft 176 for further processing, storage or disposal.

The invention having been disclosed in connection with certain preferred arrangements and embodiments, variations within the scope of the invention will now be apparent to persons skilled in the art. Reference should be made to the appended claims rather than the foregoing exemplary embodiments in order to assess the scope of the invention in which exclusive rights are claimed.

What is claimed is:

1. A measurement apparatus for determining relative proportions of at least two materials forming a liquid, the at least two materials having different densities and different light transmission properties, the apparatus comprising:
   at least once container for confining a sample of the liquid, the container being light transmissive and having an upper surface, a lower surface and an internal bore, one of said upper and lower surfaces being convex and the other being substantially flat;
   a rotor wheel having means for holding the container such that the container occupies a length extension radially of an axis of rotation of the rotor wheel, and is held radially inwardly relative to the axis, at an elongated radial opening in the rotor wheel;
   a motor coupled to the rotor wheel for rotating the rotor wheel and the container about the axis, whereby the materials of different densities are separated along the length extension due to centripetal acceleration relative to the axis, substantially to occupy different positions along the length extension, thereby forming an interface between the materials;
   at least one source of radiation arranged to illuminate said container, incident on the convex one of said upper and lower surfaces of the container, along at least a portion of the length extension;
   radiation sensing means mounted adjacent the flat one of said upper and lower surfaces of the container, operable to detect radiation from the source over a range encompassing at least a part of said portion of the length extension, the radiation sensing means comprising an elongated array of pixel elements producing a distinct signal with variation of detected radiation on opposite sides of the interface due to said different light transmission properties of the materials; and,
   indicator means responsive to the signal for displaying a relative position of the interface in the range.

2. The measurement apparatus according to claim 1, wherein the pixel elements are photodiodes defining an array, and further comprising at least one amplifier coupled to the photodiodes and to at least one threshold detector operable to compare a signal level for each of the photodiodes to a threshold level for discriminating high and low light levels.

3. The measurement apparatus according to claim 2, further comprising a digital processor and timing means responsive to the signal, operable to count pixels on at least one side of a change between high and low light levels occurring at the interface, and to calculate the percentage of the range occupied by pixels on that side relative to a total number in the range.

4. The measurement apparatus according to claim 3, wherein the indicator means comprises a numeric display operable to present the percentage.

5. The measurement apparatus according to claim 1, further comprising means operable to sense an angular position of the rotor, for triggering the radiation sensing means at a position where the opening is disposed between the source of radiation and the radiation sensing means.

6. The measurement apparatus of claim 1, wherein the container is a capillary tube cuvette that is elongated along the length extension, and has an inner diameter that is sufficiently small to retain the liquid via surface tension of the liquid, and wherein the means for holding the container includes a cuvette holder operable to seal at least a radially outer end of the cuvette, the rotor having means for engaging the cuvette holder to position the cuvette along the radial extension.

7. The measurement apparatus according to claim 6, wherein at least one end of the cuvette is shaped to define part of a spherical surface adjacent to a capillary inlet to the cuvette.

8. The measurement apparatus according to claim 1, wherein the flat surface of the container is oriented toward the radiation sensing means and the convex surface of the container is oriented toward the source of illumination, and further comprising a sensor operable to trigger the radiation sensing means at an angular position of the rotor where the container is between the source of illumination and the radiation sensing means.

9. A measurement apparatus for determining relative proportions of at least two materials forming a liquid, the at least two materials having different densities and different properties of at least one of light transmission and light reflection, the apparatus comprising:
   at least one container for confining a sample of the liquid, the container comprising a light transmissive cuvette having a fin enabling manual manipulation of the cuvette;
   a rotor wheel having means for holding the container such that the container occupies a length extension radially of an axis of rotation of the rotor wheel, and is held radially inwardly relative to the axis;
   a motor coupled to the rotor wheel for rotating the rotor wheel and the container about the axis, whereby the materials of different densities are separated along the length extension due to centripetal acceleration relative to the axis, substantially to occupy different positions along the length extension, thereby forming an interface between the materials;
   at least one source of radiation arranged to illuminate the materials in said container along at least a portion of the length extension;
   radiation sensing means operable to detect radiation from the source over a range encompassing at least a part of said portion of the length extension, the radiation sensing means producing a distinct signal with variation of detected radiation on opposite sides of the interface due to said different properties of the materials; and,
   indicator means responsive to the signal to displaying a relative position of the interface in the range.

10. The measurement apparatus according to claim 9, wherein the fin is arranged at one end of the cuvette and tapers toward the cuvette approaching an opposite end of the cuvette.

* * * * *